Figure 1:
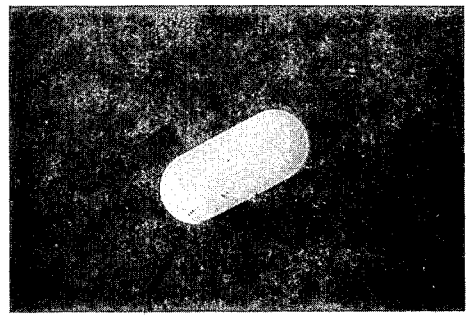

United States Patent [19]

Deutsch et al.

[11] Patent Number: 4,897,270

[45] Date of Patent: Jan. 30, 1990

[54] PHARMACEUTICAL COMPOSITIONS

[75] Inventors: David S. Deutsch, London; Jamshed Anwar, Ilford, both of United Kingdom

[73] Assignee: Glaxo Group Limited, GB2

[21] Appl. No.: 291,364

[22] Filed: Dec. 30, 1988

Related U.S. Application Data

[63] Continuation of Ser. No. 71,163, Jul. 8, 1987, abandoned, which is a continuation of Ser. No. 913,267, Sep. 30, 1986, abandoned.

[30] Foreign Application Priority Data

Sep. 30, 1985 [GB] United Kingdom ............... 8524001

[51] Int. Cl.$^4$ .................. A61K 9/28; A61K 9/36; A61K 31/71
[52] U.S. Cl. .................................. 424/465; 424/480; 514/202
[58] Field of Search ............... 424/465, 480; 514/202

[56] References Cited

U.S. PATENT DOCUMENTS

| | | | |
|---|---|---|---|
| 3,256,111 | 6/1966 | Singiser | 424/480 |
| 3,372,015 | 2/1968 | Sjogren et al. | 424/480 |
| 3,383,236 | 5/1968 | Brindamour | 424/480 |
| 3,476,588 | 11/1969 | Pitel | 424/480 |
| 3,477,864 | 11/1969 | Tuji | 424/480 |
| 3,539,380 | 11/1970 | Johnson | 424/480 |
| 3,931,404 | 1/1976 | Fulberth et al. | 424/246 |
| 3,981,984 | 9/1976 | Signorino | 424/480 |
| 4,140,764 | 2/1979 | Howarth | 424/114 |
| 4,143,129 | 3/1979 | Marsden | 424/80 |
| 4,176,175 | 11/1979 | Maekawa et al. | 424/480 |
| 4,267,320 | 5/1981 | Gregson et al. | 540/222 |
| 4,302,440 | 11/1981 | John et al. | 424/480 |
| 4,414,204 | 11/1983 | Tarcsay et al. | 424/177 |
| 4,446,317 | 5/1984 | Gregson et al. | 540/222 |
| 4,470,980 | 9/1984 | Higuchi et al. | 514/202 |
| 4,470,980 | 9/1984 | Hieguchi et al. | 424/232 |
| 4,517,179 | 5/1985 | Raghunathan | 514/249 |
| 4,562,181 | 12/1985 | Crisp et al. | 540/222 |
| 4,602,012 | 7/1986 | Weingarten | 514/202 |
| 4,609,640 | 9/1986 | Morishita et al. | 514/12 |
| 4,616,008 | 10/1986 | Hirai et al. | 514/200 |
| 4,666,886 | 5/1987 | Baschang et al. | 514/17 |
| 4,775,750 | 10/1988 | White et al. | 540/222 |
| 4,820,833 | 4/1989 | Crisp et al. | 540/222 |

FOREIGN PATENT DOCUMENTS

| | | |
|---|---|---|
| 124027 | 11/1984 | European Pat. Off. . |
| 147780 | 7/1985 | European Pat. Off. . |
| 3432984 | 3/1985 | Fed. Rep. of Germany . |
| 3633292 | 4/1987 | Fed. Rep. of Germany . |
| 2127401 | 4/1984 | United Kingdom . |
| 2145408 | 3/1985 | United Kingdom . |
| 2145409 | 2/1987 | United Kingdom . |
| 2204792 | 11/1988 | United Kingdom . |

*Primary Examiner*—Shep K. Rose
*Attorney, Agent, or Firm*—Bacon & Thomas

[57] ABSTRACT

A pharmaceutical tablet is described which comprises a tablet core containing the antibiotic cefuroxime axetil and a film coat which serves to mask the bitter taste of the cefuroxime axetil upon oral administration. It has been found that conventional film-coated tablets reduce the bioavailability of cefuroxime axetil and the invention overcomes this by control of the film coat rupture time and use of a tablet core which disintegrates immediately following rupture of the film coat.

19 Claims, 2 Drawing Sheets

Initial 5 secs 7 secs 10 secs 11 secs 12 secs 13 secs 15 secs

PHARMACEUTICAL COMPOSITIONS

This is a continuation of application Ser. No. 071,163 filed 7/8/87, which is a continuation of Ser. No. 913,267 filed 9/30/86, now abandoned.

This invention is concerned with pharmaceutical compositions containing the 1-acetoxyethyl ester of cefuroxime which has the approved name 'cefuroxime axetil'.

Cefuroxime, as disclosed in British Patent Specification No. 1453049, is a valuable broad spectrum antibiotic characterised by high activity against a wide range of gram-positive and gram-negative microorganisms, this property being enhanced by the very high stability of the compound to $\beta$-lactamases produced by a range of gram-negative microorganisms. Cefuroxime and its salts are principally of value as injectable antibiotics since they are poorly absorbed from the gastro-intestinal tract.

We have found that esterification of the carboxyl group of cefuroxime as a 1-acetoxyethyl ester to give cefuroxime axetil improves the effectiveness on oral administration as disclosed in British Pat. Specification No. 1571683. The presence of the 1-acetoxyethyl esterifying group results in significant absorption of the compound from the gastro-intestinal tract, whereupon the esterifying group is hydrolysed by enzymes present in, for example, serum and body tissues to yield the antibiotically active acid. It is particularly advantageous to employ cefuroxime axetil in an amorphous form as disclosed in British Patent Specification No. 2127401.

Cefuroxime axetil has therefore extended the valuable therapeutic potential of cefuroxime by making available a form of the antibiotic which may be administered orally rather than by injection only.

A convenient means of presenting cefuroxime axetil for oral administration is as a tablet. However, cefuroxime axetil has an extremely bitter taste which is long lasting and which cannot be adequately masked by the addition of sweeteners and flavours. In order to provide tablets of cefuroxime axetil which do not have the significant disadvantage of the bitter taste, it has been found necessary to use tablets which are film coated.

When tablets of cefuroxime axetil were film coated in conventional manner, it was found that they complied with the standard disintegration tests (with discs) specified in the British and United States Pharmacopeias [British Pharmacopeia (1980) XIIA, AII3; United States Pharmacopeia XXI, p 1243] However, it was found that when such film-coated tablets were administered to human volunteers low levels of absorption of cefuroxime axetil were obtained from the gastro-intestinal tract.

We have now discovered that cefuroxime axetil once in contact with aqueous media can form a gelatinous mass. This gelling effect is temperature dependent but does occur at temperatures of about 37° C., i.e. at the physiological temperatures at which the disintegration of orally administered tablets takes place. We have further found that, with the relatively slow permeation of moisture the film coat to the core which occurs upon administration of tablets of cefuroxime axetil provided with conventional film coats, the cefuroxime axetil present in the tablet core may gel. This gel formation leads to poor disintegration of the tablet core and hence to poor dissolution of cefuroxime axetil; thus the absorption from the gastro-intestinal tract is greatly reduced. This occurs with both the crystalline and amorphous forms of cefuroxime axetil referred to above.

We have further discovered that the problem of gelling may be overcome and the high bioavailability of cefuroxime axetil maintained by preparing a film coated tablet in which, upon contact with gastro-intestinal fluid, the film coating ruptures very rapidly and the core then immediately disintegrates thus allowing dispersion and dissolution of the cefuroxime axetil in the gastro-intestinal tract before any gelling effect can occur.

According to one feature of the invention there is thus provided a pharmaceutical tablet for oral administration which comprises a tablet core containing an effective amount of cefuroxime axetil as active ingredient and a film coat which serves to mask the bitter taste of cefuroxime axetil upon oral administration, the film coat having a rupture time of less than 40 seconds, preferably less than 25 seconds and more preferably less than 15 seconds when measured by the rupture test as herein defined and the tablet core disintegrating immediately following rupture of the film coat in the said rupture test.

Figure 2:
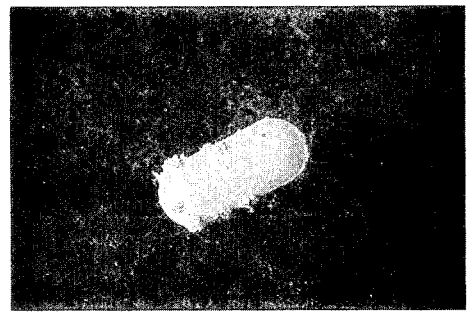
Figure 3:
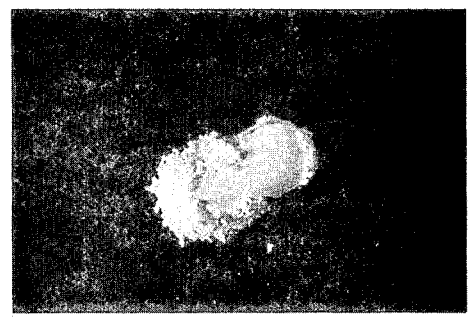
Figure 4:
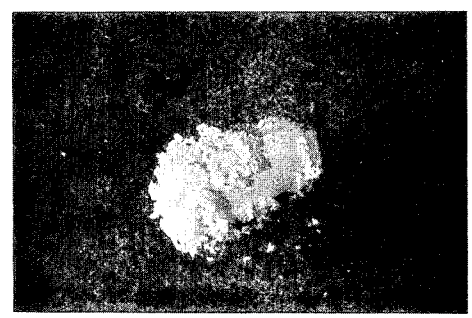
Figure 5:
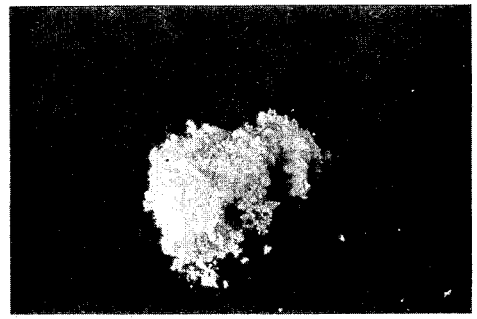
Figure 6:
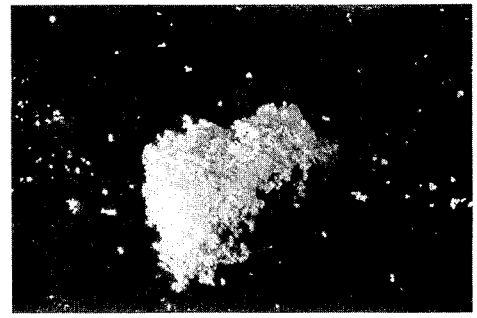
Figure 7:
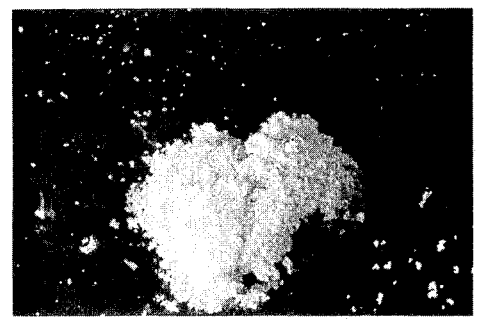
Figure 8:
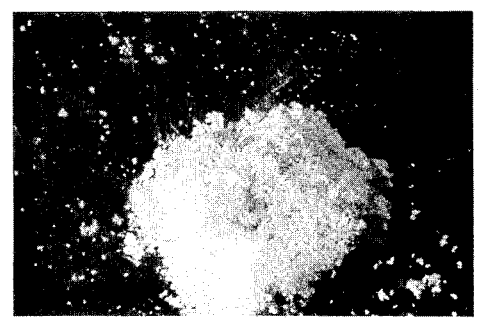

In the rupture test as herein defined the film-coated tablet is placed in a beaker of still hydrochloric acid (0.07M) at 37° C. The rupture time is measured as the time which elapses before the core of the tablet first becomes visible to the naked eye through the ruptured film coat. FIGS. 1 to 8 of the accompanying drawings illustrate the rupture of the film coat followed by the immediate disintegration of the core of a film coated tablet according to the invention having a rupture time of less than about 5 seconds.

It has been found useful to define the film coats of tablets according to the invention in terms of mean rupture times for representative batches of film coated tablets.

Thus according to a further feature of the invention there is provided a pharmaceutical tablet for oral administration which comprises a tablet core containing an effective amount of cefuroxime axetil as active ingredient and a film coat which serves to mask the bitter taste of cefuroxime axetil upon oral administration, the film coat having a mean rupture time for a batch of 20 tablets of less than 35 seconds, preferably less than 25 seconds and more preferably less than 15 seconds, when measured by the rupture test as herein defined and the tablet core disintegrating immediately following rupture of the film coat in the said rupture test.

According to a still further feature of the invention there is provided a pharmaceutical tablet for oral administration which comprises a tablet core containing an effective amount of cefuroxime axetil as active ingredient and a film coat which serves to mask the bitter taste of cefuroxime axetil upon oral administration, the film coat having a mean rupture time for a batch of 100 tablets of less than 30 seconds, preferably less than 20 seconds and more preferably less than 12 seconds, when measured by the rupture test as herein defined and the tablet core distintegrating immediately following rupture of the film coat in the said rupture test.

In order to obtain film coats which rupture rapidly in accordance with the present invention, it is preferred to apply a relatively thin coat of the film-forming composition on to the tablet core. In order to obtain tablet cores which disintegrate immediately following rupture of the film coat in the rupture test, it is convenient to incorporate into the core an effective amount of a disintegrant.

According to a yet still further feature of the invention, there is thus provided a process for the preparation of a film coated tablet according to the invention as hereinbefore defined in which a cefuroxime axetil-containing tablet core is coated with a film-forming composition, the said film-forming composition being applied in an amount whereby the rupture time of the film coated tablet is in accordance with the invention as hereinbefore defined and the tablet core containing an effective amount of a disintegrant whereby it disintegrates immediately following rupture of the film coat in the rupture test as herein defined.

The film-forming composition is preferably an aqueous solution of a water-soluble film-forming agent but solutions of film-forming agents in other solvents can if desired be used. The film-forming agent may for example be a polymeric substance with suitable film-forming properties, such polymeric substances preferably have a number average molecular weight of not more than 15,000. Film-forming agents which are useful include hydroxyalkylcelluloses (e.g. hydroxypropyl cellulose, or hydroxypropylmethylcelluloses such as hydroxypropylmethylcellulose 5 or 6 or hydroxypropylmethylcellulose 15) and other cellulose-based polymers (e.g. hydroxypropoxy and methyl ethers on cellulose substrates, such as Sepifilm 002) which may be used in both aqueous and non-aqueous solvent systems; alkylcelluloses such as methyl- or ethylcellulose, which may be used in aqueous systems; polyvinylpyrrolidone (aqueous or non-aqueous solvents); polyvinylacetate phthalate, shellac and zein (all of which require non-aqueous solvent systems); and polymer systems based on methacrylic acid and esters thereof, such as Eudragit E and Eudragit E30D. Hydroxypropylmethylcellulose 5 or 6 is particularly preferred.

The film-forming compositions may also conveniently contain excipients such as plasticisers (e.g. propylene glycol, polyethylene glycol, glycerol and sorbitol, all of which can be used in aqueous systems; glycerol triacetate, diethyl phthalate and triethyl citrate, all of which can be used in non-aqueous systems), preservatives (e.g. methyl and propyl hydroxybenzoates) and colouring agents (e.g. titanium dioxide pigments with lake colours and iron oxide pigments). The incorporation of such excipients in general reduces the film-forming compositions and this has the useful effect of also reducing the rupture time of the film coats, thereby enabling film coats of greater thickness to be used while still providing the rupture times required by the present invention. The weight of the film coats applied to tablets according to the invention is preferably in the range 1 mg per 10 to 70 mm$^2$, and more preferably 1 mg per 12 to 35 mm$^2$, of the surface area of the tablet.

The tablet core may be formulated such that it disintegrates immediately following rupture of the film coat, using methods well known in the art. This may generally be achieved by using disintegrants. Disintegrants which may be used to provide the desired disintegration properties include for example potato starch, sodium starch glycolate, defatted soybean extract, cross linked polyvinyl-pyrrolidone and cross linked carboxymethylcelluloses, with sodium carboxymethylcelluloses (croscarmellose sodium) being particularly preferred. The tablet cores conveniently comprise from 2 to 15% by weight of disintegrant, preferably from 4 to 10% by weight.

Examples of other pharmaceutically acceptable excipients which may be present in the core of the film coated tablets of the invention are binding agents, e.g. pregelatinised maize starch, polyvinylpyrrolidone and hydroxypropylmethylcelluloses such as hydroxypropylmethylcellulose 5 or 6; fillers, e.g. starch, lactose, micro-crystalline cellulose and calcium phosphates; lubricants and flow aids, e.g. hydrogenated vegetable oils, talc and silica; and wetting agents e.g. sodium lauryl sulphate.

The tablet cores may conveniently be prepared by blending together the active ingredient and the excipients, followed by compaction (for example roller compaction) to give sheets or direct compression to give tablet slugs. The compacted sheets or tablet slugs may then be broken down to produce granules. Granulation may be achieved by, for example, passing the tablet slugs or compacted sheets through a sieve or an oscillating granulator. The granules may if desired be blended with additional excipients, for example disintegrants and flow aids, before being compressed into tablet cores using for example conventional punches, to give the desired core weight.

The tablet core may be film coated with the film-forming composition using aqueous or solvent methods well known in the art. The tablets may be coated in conventional coating machines such as the Manesty Accelacota, the Driam coating machine or the Hicoater. When, for example, using a 24" Manesty Accelacota with a load of 44,000 tablets as described in Example 1 below the rate of application of the film-forming composition to the tablet core will conveniently be in the range 10 to 40 ml/min, preferably about 20 to 30 ml/min, in order to provide a preferred weight of film coat as referred to above. The temperature of the incoming air will conveniently be controlled to 40° to 70° C., preferably to 50° to 55° C. The humidity of the incoming air will conveniently be up to 30% relative humidity. It will be understood by those skilled in the art that the coating operation is controlled within the above parameters to avoid overwetting with consequent local disintegration and surface pitting and overdrying during spraying with consequent poor coverage from reduced adhesion of the dry droplets. It will be appreciated that modification of the Manesty Accelacota equipment, e.g. by changing the baffle arrangement, or the use of different equipment may change the optimum conditions for production of the film coats.

The coated tablets may be dried, for example by leaving them in the coating machine after coating or by transferring them to a drying oven or hot air drier.

The cefuroxime axetil incorporated into the tablet cores will preferably be in amorphous form, as described in British Patent Specification No 2127401.

The tablets according to the invention will preferably contain from 30–95% more preferably from 50–85% by weight of cefuroxime axetil. Each tablet core conveniently contains 50–500 mg of cefuroxime as cefuroxime axetil. Doses employed for human treatment will typically be in the range 100–3000 mg cefuroxime per day, e.g. 250 to 2000 mg cefuroxime per day for adults and 125 to 1000 mg cefuroxime per day for children, although the precise dose will depend on, inter alia, the frequency of administration.

The following Examples illustrate the invention.

The cefuroxime axetil used in the Examples was highly pure and amorphous material prepared as described in British Patent Specification No. 2127401.

Opaspray pigments are based on titanium dioxide with lake colours and were supplied by Colorcon Ltd of Orpington, Kent, United Kingdom.

All percentages herein are by weight unless otherwise specified:

EXAMPLE 1

| Tablet Core | mg/tablet |
| --- | --- |
| Cefuroxime axetil equivalent to | 125.00 mg cefuroxime |
| Microcrystalline cellulose | 47.51 |
| Croscarmellose sodium type A | 20.00 |
| Sodium lauryl sulphate | 2.25 |
| Silicon dioxide | 0.63 |
| Hydrogenated vegetable oil | 4.25 |

All the ingredients with the exception of the silicon dioxide and half of the croscarmellose sodium were blended together and compacted using a roller compactor. The compacted material was comminuted using an oscillating granulator and the resultant granules were blended with the remaining excipients and then compressed using a conventional tabletting machine.

| Film-forming composition | % w/v |
| --- | --- |
| Hydroxypropylmethylcellulose 5 or 6 | 10.00 |
| Propylene glycol | 0.60 |
| Methyl hydroxybenzoate | 0.10 |
| Opaspray white m-1-7120 | 7.00 |
| Propyl hydroxybenzoate | 0.08 |
| Distilled water to 100%. | |

The film-forming composition was prepared by dispersing the ingredients in distilled water. It was then applied to approximately 44,000 tablets in a 24" Manesty Accelacota with a target coat weight of approximately 1 mg per 27 mm$^2$ on the tablets. The rate of application of the film-forming composition was maintained in the range 20 to 30 ml/min and the temperature of the incoming air was maintained in the range 50° to 55° C. with the humidity of the incoming air not being permitted to exceed 30%. Adjustments of the rate of application and temperature of the incoming air within the above ranges were made as necessary during the course of the spraying operation to avoid either overwetting or overdrying as previously described.

Mean film coat rupture time (100 tablets)=4.9 seconds.

EXAMPLE 2

| Tablet Core | mg/tablet |
| --- | --- |
| Cefuroxime axetil equivalent to | 250.00 mg cefuroxime |
| Microcrystalline cellulose | 95.02 |
| Croscarmellose sodium type A | 40.00 |
| Sodium lauryl sulphate | 4.50 |
| Silicon dioxide | 1.25 |
| Hydrogenated vegetable oil | 8.5 |

All the ingredients with the exception of the silicon dioxide and half of the croscarmellose sodium were blended together and compacted using a roller compactor. The compacted material was comminuted using an oscillating granulator and the resultant granule was blended with the remaining excipients and then compressed using a conventional tabletting machine.

| Film-forming composition | % w/v |
| --- | --- |
| Hydroxypropylmethylcellulose 5 or 6 | 10.00 |
| Propylene glycol | 0.60 |
| Methyl hydroxybenzoate | 0.10 |
| Opaspray blue M-1-4395B | 12.00 |
| Propyl hydroxybenzoate | 0.08 |
| Distilled water to 100%. | |

The film-forming composition was prepared by dispersing the ingredients in distilled water. It was then applied to approximately 22,000 tablets in a 24" Manesty Accelacota with a target coat weight of approximately 1 mg per 32 mm$^2$ on the tablets under conditions as described in Example 1.

Mean film coat rupture time (100 tablets)=3.5 seconds.

EXAMPLE 3

| Tablet Core | mg/tablet |
| --- | --- |
| Cefuroxime axetil equivalent to | 250.00 mg cefuroxime |
| Microcrystalline cellulose | 94.55 |
| Croscarmellose sodium type A | 15.50 |
| Sodium lauryl sulphate | 4.50 |
| Silicon dioxide | 1.25 |
| Hydrogenated vegetable oil | 8.50 |

All the ingredients except the silicon dioxide are blended together and compacted using a roller compactor. The compacted material is comminuted using an oscillating granulator and the resultant granule is blended with the silicon dioxide and compressed using a conventional tabletting machine.

| Film-forming composition | % w/v |
| --- | --- |
| Hydroxypropylmethylcellulose 5 or 6 | 10.00 |
| Propylene glycol | 0.60 |
| Methyl hydroxybenxoate | 0.10 |
| Propyl hydroxybenzoate | 0.08 |
| Opaspray blue M-1-4395B | 12.00 |
| Distilled water to 100%. | |

The film coat is prepared by dispersing the ingredients in distilled water. Tablets are coated using the film coating technique described in Examples 1 and 2 with a target coat weight of approximately 1 mg per 32 mm$^2$.

EXAMPLE 4

| Tablet Core | mg/tablet |
| --- | --- |
| Cefuroxime axetil equivalent to | 500.00 mg cefuroxime |
| Microcrystalline cellulose | 190.04 |
| Croscarmellose sodium type A | 80.00 |
| Sodium lauryl sulphate | 9.00 |
| Silicon dioxide | 2.50 |
| Hydrogenated vegetable oil | 17.00 |

All the ingredients with the exception of the silicon dioxide and half of the croscarmellose sodium were blended together and compacted using a roller compactor. The compacted material was comminuted using an oscillating granulator and the resultant granule was blended with the remaining excipients and then compressed using a conventional tabletting machine.

| Film-forming composition | % w/v |
|---|---|
| Hydroxypropylmethylcellulose 5 or 6 | 10.00 |
| Propylene glycol | 0.60 |
| Methyl hydroxybenzoate | 0.10 |
| Opaspray blue M-1-4399 | 12.00 |
| Propyl hydroxybenzoate | 0.08 |
| Distilled water to 100%. | |

The film-forming composition was prepared by dispersing the ingredients in distilled water. It was then applied to approximately 11,000 tablets in a 24" Manesty Accelacota with a target coat weight of approximately 1 mg per 27 mm$^2$ on the tablets under conditions as described in Example 1.

Mean film coat rupture time (100 tablets)=2.5 seconds.

We claim:

1. A film coated pharmaceutical tablet for oral administration which comprises a tablet core containing an effective amount of cefuroxime axetil as active ingredient, an effective amount of a disintegrant to produce tablet core disintegration immediately following film coat rupture, and a film coat which serves to mask the bitter taste of cefuroxime axetil upon oral administration, the film coat having a rupture time of less than 40 seconds when measured by a rupture test wherein the tablet is placed in a beaker of still 0.07M hydrochloric acid at 37° C., the rupture time being measured as the time which elapses before the core of the tablet first becomes visible to the naked eye through the ruptured film coat; and the tablet core disintegrating immediately following rupture of the film coat in the said rupture test.

2. A pharmaceutical tablet as claimed in claim 1 wherein the film coat rupture time is less than 25 seconds.

3. A pharmaceutical tablet as claimed in claim 2 wherein the film coat rupture time is less than 15 seconds.

4. Film coated pharmaceutical tablets for oral administration each comprising a tablet core containing an effective amount of cefuroxime axetil as active ingredient, an effective amount of a disintegrant to produce tablet core disintegration immediately following film rupture, and a film coat which serves to mask the bitter taste of cefuroxime axetil upon oral administration, the film coat having a mean rupture time for a batch of 20 tablets of less than 35 seconds, when measured by a rupture test wherein the tablet is placed in a beaker of still 0.07M hydrochloric acid at 37° C., the rupture times being measured as the time which elapses before the core of the tablet first becomes visible to the naked eye through the ruptured film coat; and the tablet core disintegrating immediately following rupture of the film coat in the said rupture test.

5. A pharmaceutical tablet as claimed in claim 4 wherein the mean rupture time for a batch of 20 tablets is less than 25 seconds.

6. A pharmaceutical tablet as claimed in claim 5 wherein the mean rupture time for a batch of 20 tablets is less than 15 seconds.

7. Film coated pharmaceutical tablets for oral administration each comprising a tablet core containing an effective amount of cefuroxime axetil as active ingredient, an effective amount of a disintegrant to produce tablet core disintegration immediately following film rupture, and a film coat which serves to mask the bitter taste of cefuroxime axetil upon oral administration, the film coat having a mean rupture time for a batch of 100 tablets of less than 30 seconds when measured by a rupture test wherein the tablet is placed in a beaker of still 0.07M. hydrochloric acid at 37° C., the rupture times being measured as the time which elapses before the core of the tablet first becomes visible to the naked eye through the ruptured film coat; and the tablet core disintegrating immediately following rupture of the film coat in the said rupture test.

8. A pharmaceutical tablet as claimed in claim 7 wherein the mean rupture time for a batch of 100 tablets is less than 20 seconds.

9. A pharmaceutical tablet as claimed in claim 8 wherein the mean rupture time for a batch of 100 tablets is less than 12 seconds.

10. A pharmaceutical tablet as claimed in claim 1 wherein the film coat comprises a hydroxyalkylcellulose as a film-forming agent.

11. A pharmaceutical tablet as claimed in claim 10 wherein the film-forming agent is a hydroxypropylmethylcellulose.

12. A pharmaceutical tablet as claimed in claim 11 wherein the film-forming agent is hydroxypropylmethylcellulose 5 or 6.

13. A pharmaceutical tablet as claimed in claim 1 wherein the weight of the film coat is 1 mg per 10 to 70 mm$^2$ of the surface area of the tablet.

14. A pharmaceutical tablet as claimed in claim 13 wherein the weight of the film coat is 1 mg per 12 to 35 mm$^2$ of the surface area of the tablet.

15. A pharmaceutical tablet as claimed in claim 1 wherein the tablet core contains cefuroxime axetil in amorphous form.

16. A pharmaceutical tablet as claimed in claim 1 containing from 30 to 95% by weight of cefuroxime axetil.

17. A pharmaceutical tablet as claimed in claim 16 containing from 50 to 85% by weight of cefuroxime axetil.

18. A pharmaceutical tablet as claimed in claim 1 containing from 50 to 500 mg of cefuroxime as cefuroxime axetil in the tablet core.

19. A pharmaceutical tablet as claimed in claim 1 wherein the disintegrant comprises a cross-linked carboxymethylcellulose.

* * * * *